United States Patent [19]

Alessi et al.

[11] Patent Number: 4,895,860

[45] Date of Patent: Jan. 23, 1990

[54] NOVEL SUBSTITUTED 3H-1,2,3,5-OXATHIADIAZOLE 2-OXIDES USEFUL AS ANTHIHYPERGLYCEMIC AGENTS

[75] Inventors: Thomas R. Alessi, Monmouth Junction; John W. Ellingboe, Princeton, both of N.J.

[73] Assignee: American Home Products Corporation, New York, N.Y.

[21] Appl. No.: 341,514

[22] Filed: Apr. 21, 1989

[51] Int. Cl.$^4$ .................... C07D 291/04; A61K 31/41
[52] U.S. Cl. ...................................... 514/360; 548/122
[58] Field of Search ......................................... 548/122

[56] References Cited

U.S. PATENT DOCUMENTS 4,148,801  4/1979  Santilli ................................ 504/224

OTHER PUBLICATIONS

Eloy Bull Soc Chim Belg. 74 129 (1965).
A. Dondoni et al, J. Org. Chem., 42 (21), 3372–3377 (1977).
A. Y. Chang et al, Diabetes, 32 830–838, (1983).

Primary Examiner—Robert Gerstl
Attorney, Agent, or Firm—Walter Patton

[57] ABSTRACT

This invention relates to novel substituted 3H-1,2,3,5-oxathiadiazole 2-oxides, to the processes for their preparation, to methods for using the compounds, and to pharmaceutical compositions thereof. The compounds have pharmaceutical properties which render them beneficial for the treatment of diabetes mellitus and associated conditions.

23 Claims, No Drawings

NOVEL SUBSTITUTED 3H-1,2,3,5-OXATHIADIAZOLE 2-OXIDES USEFUL AS ANTIHIHYPERGLYCEMIC AGENTS

BACKGROUND OF THE INVENTION

This invention relates to novel substituted 3H-1,2,3,5-oxathiadiazole 2-oxides, to the processes for their preparation, to methods for using the compounds, and to pharmaceutical compositions thereof. The compounds have pharmaceutical properties which render them beneficial for the treatment of diabetes mellitus and associated conditions.

The serious complications of diabetes mellitus such as nephropathy, retinopathy, neuropathy and cataract are all associated with an excessive amount of blood glucose. The major therapeutic objective is therefore the normalization of blood glucose, both in the fasting and postprandial situations.

The therapeutic approaches to the treatment of Non-Insulin Dependent Diabetes Mellitus (NIDDM, Type II) involve the use of diet, insulin or orally active hypoglycemic agents. Presently, such agents are chosen (a) from sulfonylureas such as chloropropamide, glyburide and others or (b) biguanides such as metformin and related products. Both these groups of agents have serious disadvantages. Sulfonylureas, upon chronic treatment, lose their effectiveness. In contrast, biguanides suffer from a serious side effect, that causes lactic-acidosis.

More recently, oxazolidinedione (U.S. Pat. No. 4,342,771) and thiazolidinedione (European patent application No. 117,035) derivatives have been described as useful hypoglycemic agents. U.S. Pat. No. 4,461,902 discloses substituted 5-[(4-cyclohexyl-methoxyphenyl)-methyl]thiazolidine-2,4-diones of formula

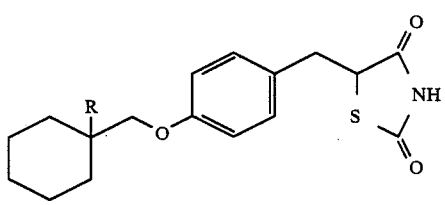

wherein R is methyl (ciglitazone) and related analogues as hypoglycemic agents.

This invention relates to substituted 3H-1,2,3,5-oxathiadiazole 2-oxides of the general formula:

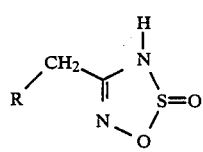

(I)

wherein R is (1)

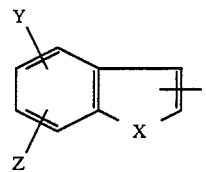

and X is NH, O, or S, and Y and Z are independently hydrogen, lower alkyl containing 1 to 6 carbon atoms, or halogen; or R is (2)

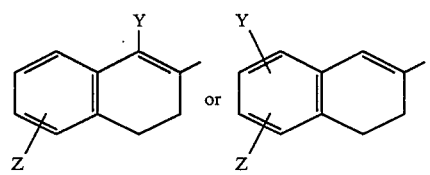

and Y and Z are as defined above; or R is (3)

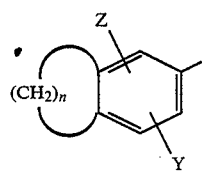

and n is 3 or 4, and Y and Z are as defined above; or R is (4)

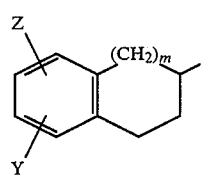

and m is 0 or 1, and Y and Z are as defined above; or R is (5)

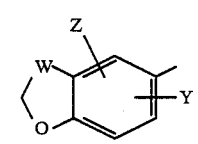

and W is $CH_2$ or O, and Y and Z are as defined above or R is cyclohexyl; and the pharmaceutically acceptable salts thereof having utility as antidiabetic agents, methods for their production and use and pharmaceutical compositions containing them.

The preferred compounds are those of formula (II)

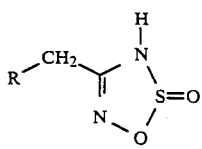

wherein R is (1)

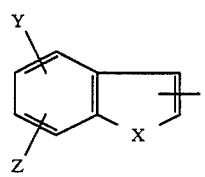

and X is NH, O, S, and Y and Z are independently hydrogen, lower alkyl containing 1 to 6 carbon atoms, or halogen; or R is (2)

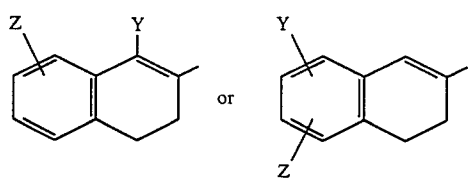

and Y and Z are as defined above, and the pharmaceutically acceptable salts thereof.

The oxathiadiazole 2-oxide portion of the compounds of the present invention can exist in more than one tautomeric form. For clarity, only one of the tautomers is represented in the generic formulas (I) and (II) above. The possible tautomeric forms are listed below:

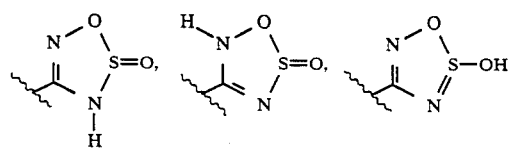

All of said tautomers are included in the present invention. The actual tautomeric form which the compounds of the present invention assume is not known.

This invention also claims mixtures of optically active isomers or partially or completely resolved isomers of the compounds disclosed.

The compounds of this invention are useful as antidiabetic agents for the reduction of blood/plasma sugar levels or for the treatment and/or prevention of diabetic complications and as antihyperlipidemic and antihyperinsulinemic agents.

The most preferred compounds of the present invention are:

4-[(1-chloro-3,4-dihydro-2-naphthalenyl)methyl]-3H-1,2,3,5-oxathiadiazole 2-oxide 4-[7-chloro-3-benzofuranyl)methyl]3H-1,2,3,5-oxathiadiazole 2-oxide;

4-[(3,4-dihydro-2-naphthalenyl)methyl]-3H-1,2,3,5-oxathiadiazole 2-oxide;

4-(1H-indol3-ylmethyl)-3H-1,2,3,5-oxathiadiazole 2-oxide;

4-[(5-bromo-1H-indol-3-yl)methyl]-3H-1,2,3,5-oxathiadiazole 2-oxide;

4-[(5-bromo-2-benzo[b]thienyl)methyl]-3H-1,2,3,5-oxathiadiazole 2-oxide;

4-[(5-fluoro-2-benzofuranyl)methyl]-3H-1,2,3,5-oxathiadiazole 2-oxide;

4-[(3-benzofuranyl)methyl]-3H-1,2,3,5-oxathiadiazole 2-oxide;

4-(cyclohexylmethyl)-3H-1,2,3,5-oxathiadiazole 2-oxide;

4-[(5-chloro-3-benzofuranyl)methyl]-3H-1,2,3,5-oxathiadiazole 2-oxide;

4-[(5-bromo-3-benzofuranyl)methyl]-3H-1,2,3,5-oxathiadiazole 2-oxide;

4-[(1,2,3,4-tetrahydro-2-naphthalenyl)methyl]-3H-1,2,3,5-oxathiadiazole 2-oxide;

4-[(6-chloro-3-benzofuranyl)methyl]-3H-1,2,3,5-oxathiadiazole 2-oxide;

4-[(5,7-dichloro-3-benzofuranyl)methyl]-3H-1,2,3,5-oxathiadiazole 2 -oxide;

4-[(5-methyl-3-benzofuranyl)methyl]3H-1,2,3,5-oxathiadiazole 2-oxide;

4-[(2,3-dihydro-1H-inden-5yl)methyl]-3H-1,2,3,5-oxathiadiazole 2-oxide;

4-[(5-chloro-2-benzo[b]thienyl)methyl]-3H-1,2,3,5-oxathiadiazole 2-oxide;

4-[(benzo[b]thien-2-ylmethyl)-3H-1,2,3,5-oxathiadiazole 2-oxide;

4-[(5-fluoro-2-benzo[b]thienyl)methyl]-3H-1,2,3,5-oxathiadiazole 2-oxide;

4-[(benzo[b]thien-3-yl)methyl]-3H-1,2,3,5-oxathiadiazole 2-oxide;

4-[(2-benzofuranyl)methyl]-3H-1,2,3,5-oxathiadiazole 2-oxide;

4-(1,3-benzodioxol-5-ylmethyl)-3H-1,2,3,5-oxathiadiazole 2-oxide;

4-[(8-bromo-3,4-dihydro-2-naphthalenyl)methyl]3H-1,2,3,5-oxathiadiazole 2-oxide;

and the pharmaceutically acceptable salts thereof.

DETAILED DESCRIPTION OF THE INVENTION

The substituted 3H-1,2,3,5-oxathiadiazole 2-oxides of this invention may be administered to mammals, for example, man, cattle or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration. For example, the compounds may be administered orally in solid form containing such excipients as starch, milk, sugar, certain types of clay and so forth. They may also be administered orally in the form of solutions or they may be injected parenterally. For parenteral administration, they may be used in the form of a sterile solution, preferably of pH 7.2–7.6, containing a pharmaceutically acceptable buffer.

The dosage of the substituted 3H-1,2,3,5-oxathiadiazole 2-oxides will vary with the form of administration and the particular compound chosen. Furthermore, it will vary with the particular host under treatment. Generally, treatment is initiated with small dosages substantially less than the optimal dose of the compound. Therefore, the dosage is increased by small increments until efficacy is obtained. In general, the compounds of this invention are most desirably administered at a concentration level that will generally afford effective results without causing any harmful or deleterious side effects.

For oral administration (or as a suppository) to an adult patient, a preferred level of dosage ranges from about 0.01 to 50 mg/kg body weight/day. For parenteral administration to an adult patient, a preferred level of dosage ranges from about 0.005 to 10 mg/kg body weight/day, once daily or divided into 2 to 4 times a week.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents, for example, magnesium stearate.

The substituted 3H-1,2,3,5-oxathiadiazole 2-oxides can also be used in combination with dietary restriction, insulin, sulfonylureas, such as chloropropamide and glyburide, biguanides, such as metformin, aldose reductase inhibitors or hypolipidemic agents to produce a beneficial effect in the treatment of diabetes mellitus. In this instance, commercially available insulin preparations or agents exemplified above are suitable. The compounds hereof can be administered sequentially or simultaneously with insulin or the above exemplified agents. Suitable methods of administration, compositions and doses of the insulin preparations or the above exemplified agents are described in medical textbooks; for instance, "Physicians' Desk Reference", 36 ed., Medical Economics Co., Oradell, N.J., U.S.A., 1982.

The compounds of the present invention are prepared according to the general sequence outlined in Scheme I below:

Scheme 1

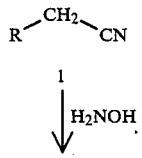

-continued
Scheme 1

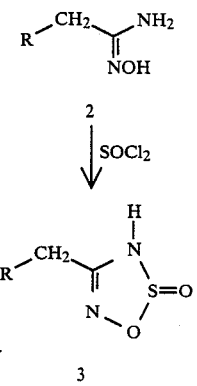

wherein R is as defined above.

All of the oxathiadiazoles 3, are prepared from the corresponding amidoximes 2, by treatment with thionyl chloride by one of two possible methods, either in the presence of an amine base, such as pyridine or triethylamine, at low temperatures ($-23°$ C. to $5°$ C.), or in the absence of base at temperatures from ambient to $110°$ C. When an amine base is used, the reaction is generally performed in inert organic solvents such as methylene chloride, acetonitrile, or tetrahydrofuran. In the absence of base, higher boiling organic solvents such as benzene or toluene are used. Reaction time ranges from a few minutes to several hours. The oxathiadiazoles are isolated either by concentration of the reaction mixture or by first washing the reaction mixture with water, separating the organic layer and drying before concentrating. Purification is effected either by chromatography on silica gel or recrystallization.

The intermediate amidoximes 2, also have activity as antidiabetic agents. They can exist as either the E or Z isomer, although the Z isomer usually predominates and is more stable. In general, the amidoximes are used without attempting to separate the isomers. The amidoximes are prepared by treatment of the corresponding nitriles 1, with hydroxylamine, the free base of which is liberated from the hydrochloride salt with either sodium methoxide, sodium ethoxide or sodium hydroxide. The reaction is performed in methanol, ethanol or aqueous dimethyl sulfoxide at temperatures ranging from ambient to reflux. The amidoximes can be isolated from the reaction mixture either by precipitation via addition of water and subsequent filtration, or by extraction into an organic solvent following removal in vacuo of the reaction solvent. Purification is effected by chromatography on silica gel or recrystallization.

The nitriles 1, required for conversion to the amidoximes, are prepared by one of the seven general methods illustrated in Schemes II-VIII below Scheme II

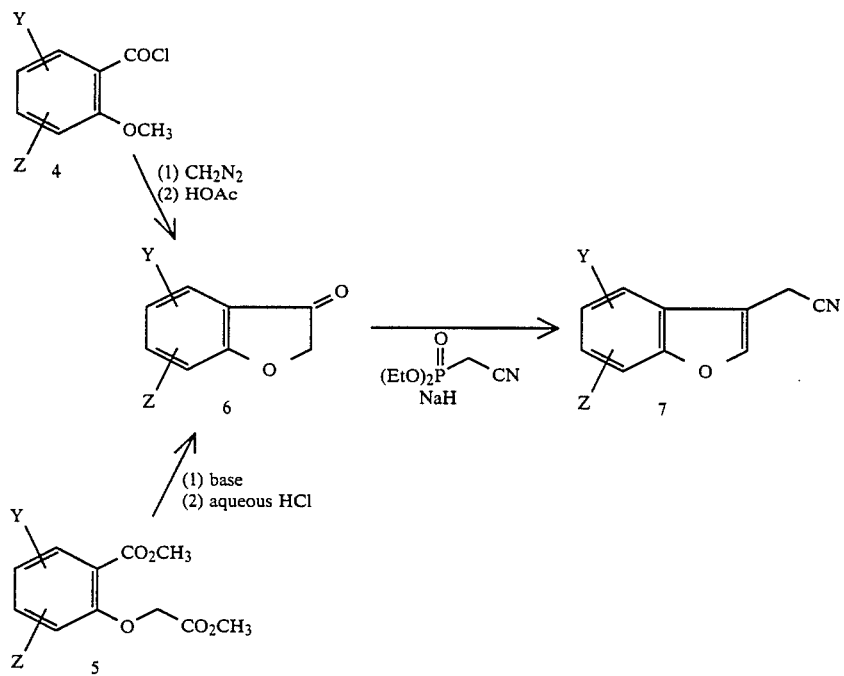

wherein Y and Z are as defined above.

Thus, the 2-methoxybenzoyl chlorides 4, are treated sequentially with diazomethane in ether, and acetic acid at ambient temperatures to yield the benzofuranones 6. Alternatively, the phenoxyacetates 5, are treated sequentially with a strong base such as sodium hydride in an inert solvent such as tetrahydrofuran or toluene at ambient temperatures to reflux, aqueous hydroxide at ambient temperatures to reflux, and aqueous hydrochloric acid to yield the benzofuranones 6. The 3-benzofuranylacetonitriles 7, are obtained by treatment of the benzofuranones 6, with a dialkyl cyanomethylphosphonate and a strong base such as sodium hydride in an inert solvent such as tetrahydrofuran or toluene at low (0° C.) to ambient temperatures.

As shown in Scheme III above the phenols or thiophenols 8, are treated with 2,3-dichloropropene 9, in the presence of a weak base such as potassium carbonate or triethylamine in a polar organic solvent such as acetone, acetonitrile, or tetrahydrofuran at ambient temperatures to reflux. The resulting allyl aryl ethers or sulfides 10, are heated to high temperatures (150° to 250° C.) in a high boiling solvent such as diethylaniline. In the case of the allyl aryl sulfides 10, (X is sulfur) the benzthiophenes 11, are obtained directly. However, conversion of the allyl aryl ethers 10 to the benzofurans 11, requires subsequent treatment with concentrated acid such as hydrochloric at ambient temperatures to 100° C. The benzthiophenes and benzofurans 11, are converted to the nitriles 12, by a two-step procedure: bromination Scheme III

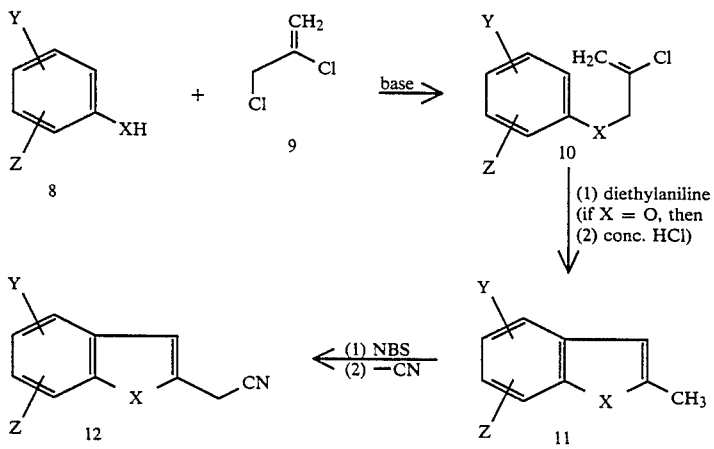

wherein X is oxygen or sulfur, and Y and Z are as defined above.

with N-bromosuccinimide in an inert solvent such as carbon tetrachloride at reflux; and treatment with lithium, sodium, or potassium cyanide in a polar solvent such as ethanol, dimethyl sulfoxide, or acetonitrile, with or without added water, at ambient temperatures to reflux.

Scheme IV

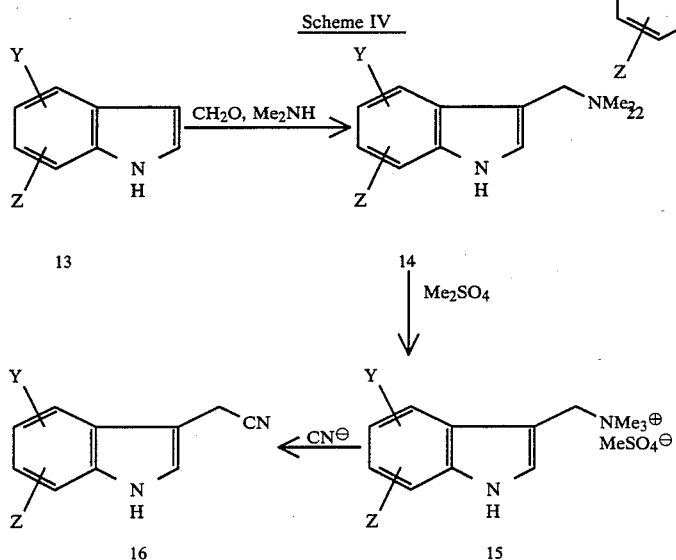

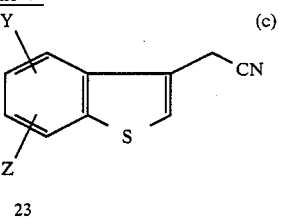

wherein Y and Z are as defined above.

As illustrated in Scheme IV, the indoles 13 are treated with formaldehyde and dimethylamine in water and acetic acid at low (0° C.) to ambient temperatures. The resulting indolymethylamines 14, are methylated with methyl sulfate in acetic acid at ambient temperatures to produce the ammonium salts 15. Treatment with lithium, sodium, or potassium cyanide in water at ambient temperatures to reflux yields the nitriles 16.

Scheme V

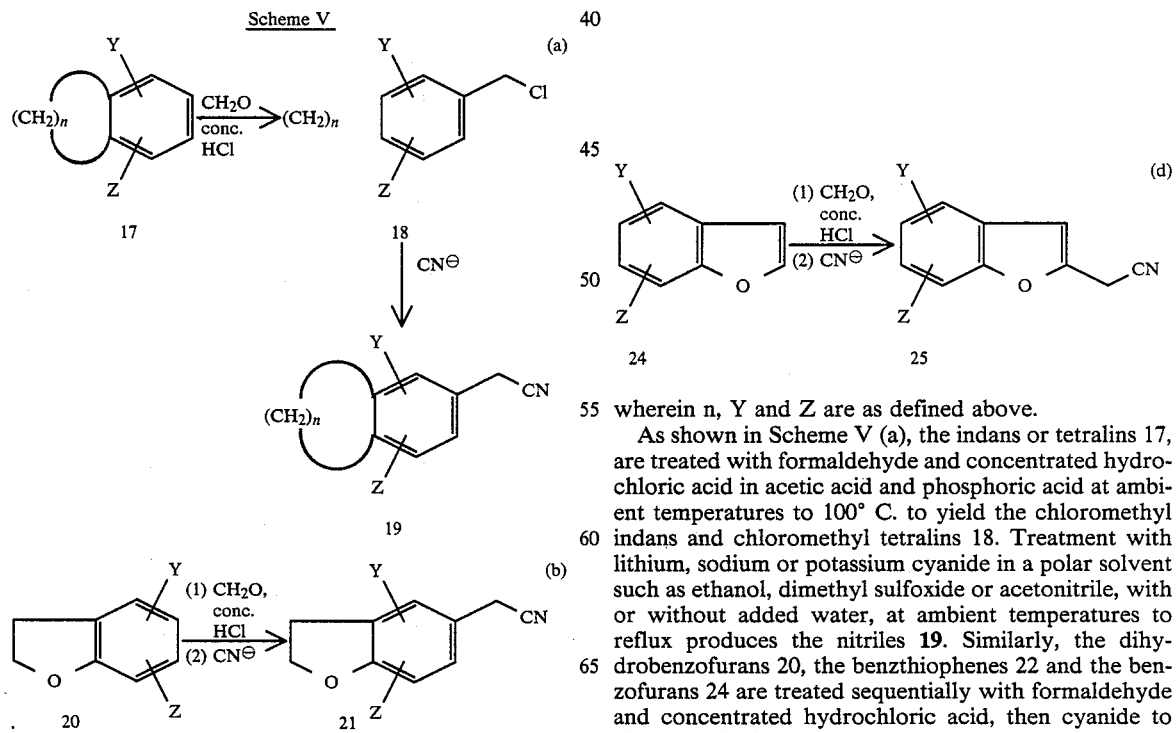

wherein n, Y and Z are as defined above.

As shown in Scheme V (a), the indans or tetralins 17, are treated with formaldehyde and concentrated hydrochloric acid in acetic acid and phosphoric acid at ambient temperatures to 100° C. to yield the chloromethyl indans and chloromethyl tetralins 18. Treatment with lithium, sodium or potassium cyanide in a polar solvent such as ethanol, dimethyl sulfoxide or acetonitrile, with or without added water, at ambient temperatures to reflux produces the nitriles 19. Similarly, the dihydrobenzofurans 20, the benzthiophenes 22 and the benzofurans 24 are treated sequentially with formaldehyde and concentrated hydrochloric acid, then cyanide to yield the nitriles 21, 23 and 25.

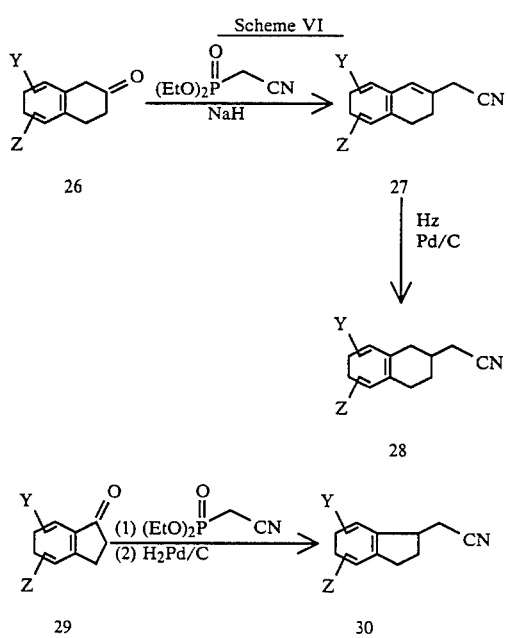

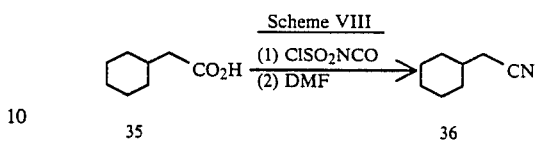

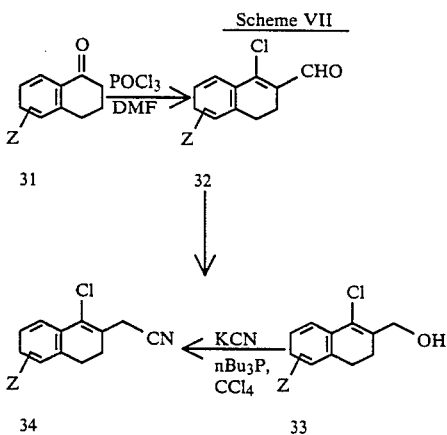

wherein Y and Z are as defined above.

As illustrated in Scheme VI (a), the 2-tetralones 26, are treated with diethyl cyanomethylphosphonate and a strong base such as sodium hydride in an inert solvent such as toluene or tetrahydrofuran at low (0° C.) to ambient temperatures to yield the dihydronaphthalenyl nitriles 27. The nitriles 27, are either used directly to prepare oxathiadiazole 2-oxides or are hydrogenated in the presence of a palladium catalyst in an organic solvent such as ethanol or ethyl acetate to produce the tetrahydronaphthalenyl nitriles 28.

Similarly, the 1-indanones 29, are treated with diethyl cyanomethylphosphonate, and the intermediates are hydrogenated to produce the nitriles 30.

wherein Z is as defined above.

As shown in Scheme VII above, the 1-tetralones 31, are treated with phosphorus oxychloride and dimethylformamide in an inert solvent such as trichloroethylene or methylene chloride at low (0° C.) to ambient temperatures. The resulting aldehyde 32, is reduced with sodium borohydride in tetrahydrofuran and an alcohol such as methanol or ethanol at low temperatures (−20° to 5° C.). Treatment of the alcohol 33, with tri-n-butyl-phosphine, carbon tetrachloride, potassium cyanide and 18-crown-6 in a solvent such as acetonitrile, tetrahydrofuran or methylene chloride at ambient temperatures to reflux yields the nitriles 34.

Finally, as illustrated in Scheme VIII, cyclohexylacetic acid is treated sequentially with chlorosulfonyl isocyanate in an inert solvent such as hexane, benzene or methylene chloride at ambient temperatures to reflux and with dimethylformamide in the same solvent at low (0° C.) to ambient temperatures to produce cyclohexylacetonitrile.

The chemical bases which are used as reagents in this invention to prepare the aforementioned pharmaceutically acceptable salts are those which form nontoxic salts with the various herein described substituted 3H-1,2,3,5-oxathiadiazole 2-oxides. These particular non-toxic base salts are of such a nature that their cations are said to be essentially non-toxic in character over the wide range of dosage administered. Examples of such cations include those of sodium, potassium, calcium and magnesium. These salts may be prepared by mixing organic solutions of the substituted 3H-1,2,3,5-oxathiadiazole 2-oxides in alcohol and the desired alkali metal alkoxide together and then isolating the resulting salts by removal of the solvent, suspension in a nonpolar solvent, and filtration. Stoichiometric quantities of reagents must be employed in order to ensure completeness of reaction and maximum production yields with respect to the desired final product.

The following examples further illustrate the present invention.

EXAMPLE 1

4-[(1-Chloro-3,4-dihydro-2-naphthalenyl)methyl]-3H-1,2,3,5-oxathiadiazole 2-Oxide Scheme VII Step (1) Preparation of 1-Chloro-2-formyl-3,4-dihydronaphthalene Phosphorus oxychloride (25.82 mL, 0.277 mol) was added dropwise to a solution of trichloroethylene (62.5 mL) and DMF (25.48 mL, 0.329 mol) keeping the temperature between 5°–10° C. -Tetralone (40 g, 0.274 mol) in trichloroethylene (62.5 mL) was added dropwise. The reaction mixture was stirred at 60° C. for 3 hours and at room temperature overnight. An aqueous sodium acetate solution (100 g/300 mL $H_2O$) was added dropwise while cooling in a water bath. The aqueous phase was extracted with ether (3×200 mL), dried ($MgSO_4$) and concentrated to give an oil (50 g). 20 g of this crude oil was chromatographed on silica gel with 50% ethyl acetate/hexane to yield 9.95 g (50%) of pure product as a white solid, m.p. 37° C.

NMR ($CDCl_3$, 200 MHz); δ 2.70 (m, 2H), 2.84 (m, 2H), 7.2–7.4 (m, 3H), 7.85 (d, J=6.2, 1H), 10.38 (s, 1H).

Step (2) Preparation of 1-Chloro-2-hydroxymethyl-3,4-dihydronaphthalene

To a mixture of sodium borohydride (2.83 g, 0.075 mol) in methanol (150 mL) at 0° C., was added dropwise a solution of 1-chloro-2-formyl-3,4-dihydronaphthalene (9.59 g, 0.05 mol) in dry THF (150 mL). The reaction was stirred at room temperature for 1 hour, carbon dioxide was cautiously bubbled through the reaction mixture for 15 minutes, and the resulting mixture was concentrated under reduced pressure. The residue was diluted with water (150 mL), extracted with ether (3×150 mL), dried ($MgSO_4$) and concentrated to give 9.95 g (102%) of product as a yellow oil.

NMR ($CDCl_3$, 200 MHz): δ 1.63 (br s, 1H), 2.6 (t, 2H), 2.85 (t, 2H), 4.50 (s, 2H), 7.05–7.3 (m, 3H), 7.63 (d, J=8.6, 1H).

Step (3) Preparation of 1-Chloro-3,4-dihydro-2-naphthalenylacetonitrile

According to the procedure of A. Mizuno et al., Synthesis 1007, (1980), a mixture of powdered KCN (5.99 g, 0.092 mol) and 18-crown-6 (1.22 g, 4.6 mmol) in acetonitrile (90 mL) was added to a mixture of 1-chloro-2-hydroxymethyl-3,4-dihydronaphthalene (8.9 g, 0.046 mol) and tri-n-butylphosphine (12.71 mL, 0.051 mol) in acetonitrile (45 mL). The resulting mixture was cooled to 0° C., and a solution of carbon tetrachloride (4.92 mL, 0.051 mol) in acetonitrile (45 mL) was added dropwise. The reaction was stirred at room temperature overnight, diluted with ether (300 mL), washed with water (300 mL), saturated $NaHCO_3$ solution (200 mL) and brine. The organic phase was dried ($MgSO_4$) and concentrated to give a brown oil. The oil was chromatographed on silica gel (eluted with 10%, 20%, 25% ethyl acetate/hexane) to yield 2.11 g (23%) of product as a yellow oil.

NMR ($CDCl_3$, 200 MHz): δ 2.61 (t, 2H), 2.95 (t, 2H), 3.61 (s, 2H), 7.12–7.35 (m, 3H), 7.61 (m, 1H).

Step (4) Preparation of N'-Hydroxy-(1-chloro-3,4-dihydro-2-naphthalenyl)ethanimidamide To a solution of sodium methoxide (6.40 mL, 0.028 mol 25 wt%/methanol) in methanol (40 mL) was added powdered hydroxylamine hydrochloride (0.95 g, 0.028 mol). The mixture was stirred at reflux for 1 hour. 1-Chloro-3,4-dihydro-2-naphthalenylacetonitrile (0.88 g, 0.014 mol) in methanol (13 mL) was added, and the reaction was stirred at room temperature for 3 days. The reaction mixture was concentrated under reduced pressure, diluted with water (50 mL), extracted with ether (3×50 mL). The organics were dried ($MgSO_4$), and concentrated to obtain a yellow froth. The froth was chromatographed on silica gel 1% MeOH/$CH_2Cl_2$) to yield 1.6 g (49%) of product as a pale green solid.

NMR ($CDCl_3$, 200 MHz): δ 2.47 (t, 2H), 2.83 (t, 2H), 3.34 (s, 2H), 4.68 (br s, 2H), 7.1–7.35 (m, 3H), 7.62 (d, J=7.0, 1H).

Step (5) Preparation of 4-[(1-Chloro-3,4-dihydro-2-naphthalenyl)methyl]-3H-1,2,3,5-oxathiadiazole 2-Oxide Thionyl chloride (0.55 mL, 7.5 mmol) was added dropwise to a mixture of N'-hydroxy-(1-chloro-3,4-dihydro-2-naphthalenyl)ethanimidamide (1.6 g, 6.8 mmol) and pyridine (1.10 mL, 13.6 mmol) in dry $CH_2Cl_2$ (25 mL) at 0° C. After the addition, the reaction was concentrated under reduced pressure, diluted with water (50 mL), and extracted with ether (3×50 mL). The organics were washed with brine, dried ($MgSO_4$), and concentrated to obtain a black froth. The froth was chromatographed on silica gel (twice: eluant 4% MeOH/$CH_3Cl_2$ and eluant 2% MeOH/$CH_2Cl_2$) to yield 612 mg (32%) of an off-white solid, m.p. 90.5°–91.5° C.

NMR ($CDCl_3$, 200 MHz): δ 2.45 (t, 2H), 2.83 (t, 2H), 3.79 (s, 2H), 7.1–7.3 (m, 3H), 7.62 (m, 1H).

MS(m/e): 282, 183, 141.

Anal. Calcd. for $C_{12}H_{11}ClN_2O_2S$: C,50.98; H, 3.92; N, 9.91%. Found: C, 51.09; H, 4.14; N, 9.83%.

EXAMPLE 2

4-[(7-Chloro-3-benzofuranyl)methyl]-3H-1,2,3,5-oxothiadiazole 2-Oxide

Scheme II

Step (1) Preparation of Methyl (Methyl 3-Chlorosalicylyl)acetate

A mixture of 3-chlorosalicylic acid (20.2 g, 0.117 mol), $Na_2SO_4$ (5.0 g, 0.035 mol), MeOH (100 mL), and saturated methanolic HCl (40 mL) was heated under reflux for 2 days. The mixture was filtered, concentrated, and partitioned between ether and $H_2O$. The organic phase was washed with saturated aqueous $NaHCO_3$, dried ($MgSO_4$) and concentrated to give a yellow oil (17.4 g). A mixture of methyl 3-chlorosalicylate (17.4 g, 0.093 mol), $K_2CO_3$ (12.9 g, 0.093 mol), and acetone (100 mL) was heated for 10 minutes. Additional acetone (100 mL) and methyl bromoacetate (14.3 g, 0.093 mol) were added and heating was continued for 18 hours. The mixture was cooled, concentrated, and partitioned between ether and $H_2O$. The organic phase was dried ($MgSO_4$) and concentrated to give a pale yellow oil (24.6 g, 80%).

NMR ($CDCl_3$, 200 MHz): δ 3.84 (s, 3H), 3.90 (s, 3H), 4.72 (s, 2H), 7.15 (dd, J=8.0, 8.0, 1H), 7.56 (d, J=8.0, 1H), 7.71 (d, J=8.0, 1H).

Step (2) Preparation of 2-Carbomethoxy-7-chloro-3-hydroxybenzofuran

According to the procedure of D. C. Schroeder, et al., J. Org. Chem., 27, 586 (1962) to a stirred suspension of NaH (50% dispersion in mineral oil, washed with hexane) (4.5 g, 0.093 mol) in THF (20 mL) was added a solution of methyl (methyl 3-chlorosalicylyl)acetate (24.1 g, 0.093 mol) in THF (50 mL). Additional THF (60 mL) was added. After 1 hour, the mixture was heated under reflux for 1 hour, cooled, and partitioned between ether and $H_2O$. The aqueous phase was acidified with 1N HCl and the precipitate was collected by filtration. This material was dissolved in ether. The solution was washed with $H_2O$, dried ($MgSO_4$), and concentrated to give a yellow solid (16.9 g, 80%).

NMR ($CDCl_3$, 200 MHz): δ 4.03 (s, 3H), 7.24 (dd, J=7.7, 7.7, 1H), 7.52 (dd, J=7.7, 1.3, 1H), 7.65 (dd, J=7.7, 1.3, 1H), 8.13 (br s, 1H).

Step (3) Preparation of 7-Chlorobenzofuran-3-one

According to the procedure of D. C. Schroeder, et al., J Org. Chem., 27, 586 (1962) a mixture of 2-carbomethoxy-7-chloro-3-hydroxybenzofuran (16.9 g, 0.075 mol), dioxane 75 mL), and 1N NaOH (375 mL, 0.375 mol) was stirred at room temperature for 2 days. The dioxane was removed under reduced pressure and the mixture was left standing for another day. Acidification with 2N HCl (270 mL, slowly) and filtration of the resulting precipitate gave a yellow solid (12.6 g). NMR analysis showed this material to be a 3:1 mixture of product and starting material. Purification by preparative HPLC gave a yellow solid (5.8 g, 46%), m.p. 108°–111° C.

NMR ($CDCl_3$, 200 MHz): δ 4.74 (s, 2H), 7.07 (dd, J=7.5, 7.5, 1H), 7.59 (dd, J=7.5, 1.3, 1H), 7.64 (dd, J=7.5, 1.3, 1H).

Step (4) Preparation of 7-Chloro-3-benzofuranylacetonitrile

To a stirred suspension of NaH 50% dispersion in mineral oil, washed with hexane; 1.82 g, 0.0378 mol) in THF (70 mL) was added a solution of diethyl cyanomethylphosphonate (6.7 g, 0.0378 mol) in THF (30 mL) dropwise over 20 minutes. After 20 minutes, the mixture was cooled to 0° C. and a solution of 7-chlorobenzofuran-3-one (5.8 g, 0.0344 mol) in THF (80 mL) was added dropwise over 30 minutes. The cooling bath was removed and stirring was continued at room temperature overnight. $H_2O$ (400 mL) and ether were added. The organic phase was washed with saturated aqueous NaCl, dried ($MgSO_4$), and concentrated to give a red solid (6.4 g, 97%).

NMR ($CDCl_3$, 200 MHz): δ 3.77 (s, 2H), 7.26 (dd, J=7.5, 7.5, 1H), 7.39 (dd, J=7.5, 1.2, 1H), 7.50 (dd, J=7.5, 1.2, 1H), 7.74 (s, 1H).

Step (5) Preparation of N'-Hydroxy-(7-chloro-3-benzofuranyl)ethanimidamide

A stirred mixture of NaOMe (25 wt % in MeOH, 11.3 mL, 0.0493 mol), MeOH (40 mL), and hydroxylamine hydrochloride (3.4 g, 0.0493 mol) was heated under reflux for 1 hour. 7-Chloro-3-benzofuranylacetonitrile (6.3 g, 0.0329 mol) and MeOH (15 mL) were added and heating was continued for 2 days. The mixture was concentrated, suspended in $H_2O$, and filtered. The solid was triturated with ether to give the product (5.4 g, 73%) as a tan solid, m.p. 142°–145° C.

NMR (DMSO-$d_6$, 200 MHz): δ 3.38 (s, 2H), 5.46 (s, 2H), 7.28 (dd, J=7.5, 7.5, 1H), 7.40 (d, J=7.5, 1H), 7.62 (d, J=7.5, 1H), 7.93 (d, 1H), 8.95 (s, 1H).

Step (6) Preparation of 4-[(7-Chloro-3-benzofuranyl)methyl]-3H-1,2,3,5-oxathiadiazole 2-Oxide To a cooled (0° C.), stirred solution of N'-hydroxy-(7-chloro-3-benzofuranyl)ethanimidamide (5.4 g, 0.0240 mol) and pyridine (3.8, 0.0480 mol) in $CH_2Cl_2$ (50 mL) was added a solution of thionyl chloride (3.1 g, 0.0264 mol) in $CH_2Cl_2$ (25 mL) over 25 minutes. Stirring was continued for an additional 20 minutes, and the mixture was concentrated, suspended in $H_2O$, and filtered. Purification by flash chromatography (eluant 25% EtOAc/hexane) and recrystallization from ethanol gave beige needles (975 mg, 15%) m.p. 160°–162° C.

NMR (DMSO-$d_6$, 400 MHz): δ 4.10 (s, 2H), 7.29 (dd, J=7.8, 7.8, 1H), 7.45 (dd, J=7.8, 0.7, 1H), 7.58 (dd, J=7.8, 0.7, 1H), 8.07 (s, 1H), 11.50 (br s, 1H).

IR(KBr, cm$^{-1}$) 3180 (NH).

MS(m/e); 270 (8%), 165 (100%).

Anal. Calcd. for $C_{10}H_7ClN_2O_3S$: C, 44.37; H, 2.61; N, 10.35%. Found: C, 44.36; H, 2.69; N, 10.24%.

EXAMPLE 3

4-[(3,4-Dihydro-2-naphthalenyl)methyl]-3H-1,2,3,5-oxathiadiazole 2-Oxide

Scheme 6

Step (1) Preparation of 3,4-Dihydro-2-naphthalenylacetonitrile

To a mechanically stirred mixture of hexane washed sodium hydride (8.98 g, 0.187 mol, 50%/mineral oil) in THF (400 mL) was added diethyl cyanomethylphosphonate (33.13 g, 0.187 mol) dropwise. The reaction was stirred at room temperature for 1/2 hour. β-Tetralone (24.8 g, 0.170 mol) in THF (100 mL) was added dropwise at 0° C., and the reaction was stirred at room temperature for 1 hour. The reaction was diluted with water (600 mL) and extracted with ether (3×400 mL). The organic phase was washed with brine, dried ($MgSO_4$), and concentrated under reduced pressure to give an orange oil. Distillation from bulb to bulb under high vacuum yielded 22.65 g (79%) of product as a pale yellow oil.

NMR ($CDCl_3$, 200 MHz): δ 2.34 (t, 2H), 2.9 (t, 2H), 3.28 (s, 2H), 6.57 (s, 1H), 7.18 (m, 4H).

Step (2) Preparation of N'-Hydroxy-(3,4-dihydro-2-naphthalenyl)ethanimidamide

To a solution of sodium methoxide (24.69 mL, 0.108 mol, 25 wt %/methanol) in methanol (135 mL) was added powdered hydroxylamine hydrochloride (8.27 g, 0.119 mol). The mixture was heated to reflux for 1/2 hour. 3,4-Dihydro-2-naphthalenylacetonitrile (9.14 g, 0.054 mol) in methanol (42 mL) was added, and refluxing was continued overnight. The solvent was removed under reduced pressure, the solid suspended in water (120 mL), extracted with ether (3×120 mL), dried ($MgSO_4$), and concentrated under reduced pressure to give a frothy oil. The oil was purified by flash chromatography (eluant 3% MeOH/$CH_2Cl_2$) to yield 6.7 g (61.1%) of product as a green solid.

NMR ($CDCl_3$, 200 MHz): δ 2.25 (t, 2H), 2.81 (t,2H), 3.02 (s, 2H), 4.62 (br s, 2H), 6.39 (s, 1H), 7.10 (m, 4H).

Step (3) Preparation of 4-[(3,4-Dihydro-2-naphthalenyl)methyl]-3H-1,2,3,5-oxathiadiazole 2-Oxide Thionyl chloride (2.55 mL, 0.035 mol) was added dropwise to a mixture of N'-hydroxy-(3,4-dihydro-2-naphthalenyl)ethanimidamide (6.5 g, 0.032 mol) and pyridine (5.18 mL, 0.064 mol) in dry $CH_2Cl_2$ (100 mL) at 0° C. After the addition, the reaction mixture was concentrated under reduced pressure, placed in an ice bath, diluted with water (50 mL), extracted with ether (3×50 mL), filtered, dried ($MgSO_4$), and concentrated under reduced pressure to give a red brown solid. The solid was triturated three times with ether (50 mL) and recrystallized from ether (75 mL) to yield 1.14 g (14.4%) of pure product as tan crystals, m.p. 118°–120.5° C.

NMR ($CDCl_3$, 200 MHz): δ 2.28 (t, 2H), 2.85 (t, 2H), 3.48 (q, 2H), 6.47 (s, 1H), 7.27 (m, 4H). MS (m/e): 249 [M+H].

Anal. Calcd. for $C_{12}H_{12}N_2O_2S$: C, 58.04; H, 4.87; N, 11.28%. Found: C, 58.00; H, 5.20; N, 11.21%.

EXAMPLE 4

4-(1H-Indol-3-ylmethyl)-3H-1,2,3,5-oxathiadiazole 2-Oxide

Scheme I

Step (1) Preparation of N'-Hydroxy-(1H-3-indolyl)ethanimidamide

According to Scheme I, 3-indolylacetonitrile (5.0 g, 0.032 mol) was converted to 3.32 g, 53% of desired product as an off-white solid.

NMR ($CDCl_3$, 200 MHz): δ 3.35 (s, 2H), 5.18 (s, 2H), 7.0 (m, 2H), 7.2 (s, 1H), 7.31 (d, J=4.0, 1H), 7.57 (d, J=6.0, 1H), 8.8 (s, 1H), 10.82 (br s, 1H).

Step (2) Preparation of 4-(1H-Indol-3-ylmethyl)-3H-1,2,3,5-oxathiadiazole 2-Oxide According to Scheme I, N'-hydroxy-(1H-3-indolyl)ethanimidamide (3.3 g, 0.0174 mol) was converted to 348 mg (8.5%) of pure product as an off-white solid, m.p. 125° C. (dec.).

NMR ($CDCl_3$, 200 MHz): δ 4.00 (s, 2H), 7.03 (m, 2H), 7.29 (s, 1H), 7.34 (d, J=7.9, 1H), 7.49 (d, J=8.1, 1H), 11.0 (s, 1H), 11.27 (s, 1H)

MS (m/e): 236 (M+H).

Anal. Calcd. for C$_{10}$H$_9$N$_3$O$_2$S:C, 51.05; H, 3.86; N, 17.86%. Found: C, 50.94; H, 4.00; N, 18.04%.

EXAMPLE 5

4-[(5-Bromo-1H-indol-3-yl)methyl]-3H-1,2,3,5-oxathiadiazole 2-Oxide

Scheme IV

Step (1) Preparation of 5-Bromo-3-(dimethylaminomethyl)indole

According to A. Ek, et al., J Am. Chem. Soc., 76, 5579 (1954), to an ice-cooled mixture of dioxane (130 mL) acetic acid (130 mL), 37% aqueous formaldehyde (9.9 mL, 0.133 mol), 40% aqueous dimethylamine (17.6 mL, 0.140 mol), and H$_2$O (10.6 mL) was added a solution of 5-bromoindole (25.0 g, 0.128 mol) in dioxane (130 mL) over 35 minutes. The internal temperature was maintained at 5° C. during the addition. After 2 hours, the cooling bath was removed and stirring was continued at room temperature overnight. The mixture was diluted with H$_2$O (1600 mL), charcoal and celite were added and the mixture was filtered. 2.5 N NaOH (1000 mL) was added and the resulting precipitate was collected by filtration to yield 98% of product as a white solid.

NMR (CDCl$_3$, 200 MHz): δ 2.27 (s, 6H), 3.57 (s, 2H), 7.10 (d, J=2.2, 1H), 7.23 (m, 2H), 7.84 (d, J=1.2, 1H), 8.37 (br s, 1H).

Step (2) Preparation of (5-Bromo-3-indolylmethyl)-trimethylammonium Methyl Sulfate According to the procedure of C. Huebner et al., J. Am. Chem. Soc., 75, 5887 (1953), a solution of 5-bromo-3-(dimethylaminomethyl)indole (28.3 g, 0.11 mol) and acetic acid (1.60 mL, 0.028 mol) in dry THF (154 mL) was added dropwise over a 1/2 hour period to a solution of dimethyl sulfate (52.04 mL, 0.55 mol) and acetic acid (1.60 mL, 0.028 mol) in dry THF (62 mL), keeping the temperature between 10°-15° C. The reaction was cooled in an ice bath for 1 hour, filtered, washed thoroughly with ether, and air dried for 1 hour to yield 41.6 g (100%) of product as a white solid. This was used immediately in the next step.

Step (3) Preparation of 5-Bromo-3-indolylacetonitrile

According to the procedure of C. Huebner et al., J. Am. Chem. Soc., 75, 5887 (1953), (5-bromo-3-indolylmethyl)-trimethylammonium methyl sulfate (41.6 g, 0.11 mol) was added to a solution of potassium cyanide (21.49 g, 0.33 mol) in water (215 mL) and stirred at 60°-70° C. for 1 hour. The reaction was cooled to room temperature, extracted with ether (2×400 mL), washed with saturated NaHCO$_3$, brine, dried (MgSO$_4$), and concentrated under reduced pressure to yield 23.4 g (90%) of product as a white solid.

NMR (CDCl$_3$, 200 MHz): δ 3.78 (s, 2H), 7.2–7.4 (m, 3H), 7.69 (s, 1H), 8.25 (br s, 1H).

Step (4) Preparation of N'-Hydroxy-(5-bromo-1H-3-indolyl)ethanimidamide

To a solution of sodium methoxide (16.92 mL, 0.074 mol, 25 wt %/methanol) in methanol (120 mL) was added powdered hydroxylamine hydrochloride (5.66 g, 0.0814 mol). The mixture was heated at reflux for 1 hour. 5-Bromo-3-indolylacetonitrile (8.8 g, 0.37 mol) was added and refluxing was continued overnight. Refluxing was continued for a further 3 hours. The reaction was cooled to room temperature and concentrated under reduced pressure to obtain a pale yellow solid. The solid was suspended in water (100 mL), stirred for ½ hour, filtered, air dried and stirred in ether (40 mL) to give 7.91 g (71%) of product as a white solid.

NMR (DMSO-d$_6$, 200 MHz): δ 3.34 (s, 2H), 5.29 (s, 2H), 7.11–7.31 (m, 3H), 7.72 (s, 1H), 8.86 (s, 1H), 11.04 (s, 1H).

Step (5) Preparation of 4-[(5-Bromo-1H-indol-3-yl)methyl]-3H-1,2,3,5-oxathiadiazole 2-Oxide Thionyl chloride (2.48 mL, 0.034 mol) was added dropwise to a mixture of N'-hydroxy-(5-bromo-1-3-indolyl)ethanimidamide (9.25 g, 0.031 mol) and pyridine (5.01 mL, 0.062 mol) in dry CH$_2$Cl$_2$ (150 mL) at 0° C. After the addition, the reaction mixture was concentrated under reduced pressure, diluted with water (100 mL), extracted with ether (3×150 mL), dried (MgSO$_4$), and concentrated to produce a green froth. Recrystallization from 2% methanol/methylene chloride (3 mL) yielded 1.25 g (12.8%) of pure product as beige crystals, m.p. 126° C. (dec.).

NMR (DMSO-d$_6$, 200 MHz): δ 4.04 (s, 2H), 7.19–7.38 (m, 3H), 7.74 (s, 1H), 11.26 (s, 1H), 11.34 (s, 1H).

MS (m/e): 313.

Anal. Calcd. for C$_{10}$H$_8$BrN$_3$O$_2$S: C, 38.23; H, 2.57; N, 13.38%. Found: C, 38.08; H, 2.54; N, 13.27%.

EXAMPLE 6

4-[(5-Bromo-2-benzothiophenyl)methyl]-3H-1,2,3,5-oxathiadiazole 2-Oxide

Scheme 3

Step (1) Preparation of 3-(4-Bromothiophenoxy)-2-chloro-1-propene

According to the procedure of W. K. Anderson et al., J. Chem. Soc., Perkin 1, 1 (1976) a mixture of 4-bromothiophenol (40.0 g, 0.211 mol) and K$_2$CO$_3$ (35.3 g, 0.254 mol) was heated at reflux for 1 hour. 2,3-Dichloro-1-propene (23.5 g, 0.211 mol) was added. The resulting mixture was heated at reflux for 2 hours, cooled and concentrated. The mixture was diluted with H$_2$O and extracted with ether (3×150 mL). The combined extracts were dried (MgSO$_4$), and concentrated to give an oil. Distillation under high vacuum gave 37.2 g (67%) of product as a colorless liquid.

NMR (CDCl$_3$, 200 MHz): δ 3.73 (s, 2H), 5.39 (s, 2H), 7.29 (dd, J=8.0, 1.2, 2H), 7.47 (dd, J=8.0, 1.2, 2H).

Step (2) Preparation of 5-Bromo-2-methylbenzthiophene

According to the procedure of W. K. Anderson, J. Chem. Soc., Perkin, 1, 1 (1976), a mixture of 3-(4-bromothiophenoxy)-2-chloro-1-propene (37.4 g, 0.142 mol) and N,N-diethylaniline (180 mL) was heated to 210°-215° C. for 2 days, cooled, and diluted with ether. The ethereal layer was washed with 10% HCl (3×200 mL), dried (MgSO$_4$), and concentrated. Purification by column chromatography (eluant: hexane) gave 15.0 g (46%) of product as a white solid.

NMR (CDCl$_3$, 200 MHz): δ 2.60 (s, 3H), 6.91 (s, 1H), 7.35 (dd, J=8.6, 1.9, 1H), 7.61 (d, J=8.6, 1H), 7.79 (d, J=1.9, 1H).

Step (3) Preparation of 2-Bromomethyl-5-bromobenzthiophene

According to the procedure of S. Gronowitz, et al., Synth. Commin., 6, (7), 475 (1976), to a stirred, boiling partial solution of N-bromosuccinimide (17.63 g, 0.099 mol) in CCl$_4$ (200 mL) was added 2,2'-azobis-(2-methylpropionitrile) (1.1 g, 0.007 mol). After one minute, a solution of 5-bromo-2-methylbenzthiophene (15.0 g, 0.066 mol) in CCl$_4$ (100 mL) was added. The resulting mixture was heated at reflux for 2 hours and cooled to 0° C. The solid was filtered. The filtrate was concentrated to give 18.19 g (90%) of product as an orange solid.

NMR (CDCl$_3$, 200 MHz): δ 4.78 (s, 2H), 6.98 (s, 1H), 7.48 (dd, J=8.3, 1.9, 1H), 7.64 (d, J=8.3, 1H), 7.87 (d, J=1.9, 1H).

Step (4) Preparation of 5-Bromo-2-benzthiophenylacetonitrile

According to the procedure of S. Gronowitz et al., Synth. Commun., 6, (7), 475 (1976), to a stirred mixture of 2-bromomethyl-5-bromobenzthiophene (23.7 g, 0.077 mol), tetrabutylammonium hydrogen sulfate (13.15 g, 0.039 mol), and sodium cyanide (4.94 g, 0.101 mol) in CHCl$_3$ (150 mL) was added a solution of KOH (2.17 g, 0.039 mol) in H$_2$O (150 mL). The resulting mixture was stirred at room temperature for 2 days. The mixture was extracted with CHCl$_3$ and the extracts were washed with 10% HCl, H$_2$O, saturated NaHCO$_3$, and saturated NaCl. The organic layer was dried (MgSO$_4$) and concentrated to give 7.00 g (36%) of product as a solid.

NMR (CDCl$_3$, 200 MHz): δ 3.75 (s, 2H), 6.98 (s,1H), 7.48 (dd, J=8.3, 1.9, 1H), 7.64 (d, J=8.3, 1H), 7.88 (d, J=1.9, 1H)

IR (CHCl$_3$, cm$^{-1}$): 2230.

Step (5) Preparation of N'-Hydroxy-(5-bromo-2-benzthiophenyl)ethanimidamide

To a stirred solution of hydroxylamine hydrochloride (3.86 g, 0.056 mol) in MeOH (100 mL) was added sodium methoxide (25 wt % in MeOH, 10.33 g, 0.056 mol). Stirring was continued for 15 minutes and 5-bromo-2-benzthiophenylacetonitrile (7.0 g, 0.028 mol) was added. The resulting mixture was refluxed for 2 days, cooled, and concentrated. The residue was diluted with H$_2$O. The solid was collected by filtration, purified by column chromatography (eluant: EtOAc/hexane, 2:3) to give 4.0 g (50%) of product as a white solid.

NMR (DMSO-d$_6$, 200 MHz): δ 3.58 (s, 2H), 5.55 (s, 2H), 7.21 (s, 1H), 7.40 (dd, J=8.3, 1.9, 1H), 7.85 (d, J=8.3, 1H), 7.98 (d, J=1.9, 1H).

Step (6) Preparation of 4-[(5-Bromo-2-benzthiophenyl)-methyl]-3H-1,2,3,5-oxathiadiazole 2-Oxide To a stirred, cooled (0° C.) mixture of N'-hydroxy-(5-bromo-2-benzthiophenyl)ethanimidamide (400 g, 0.014 mol) and pyridine (2.20 g, 0.028 mol) in CH$_2$Cl$_2$ (50 mL) was added a solution of thionyl chloride (2.0 g, 0.017 mol) in CH$_2$Cl$_2$ (10 mL). The resulting mixture was stirred for 15 minutes, concentrated, and diluted with H$_2$O. The solid was collected by filtration. Purification by column chromatography (eluant: EtOAc/hexane 1:1) gave 0.25 g (6%) of product as an orange solid, m.p. 156°–157° C.

NMR (DMSO-d$_6$, 400 MHz): δ 4.26 (s, 2H), 7.32 (s, 1H), 7.44 (dd, J=8.6, 1.9, 1H), 7.91 (d, J=8.6, 1H), 8.06 (d, J=1.9, 1H), 12.53 (s, 1H).

IR (KBr, cm$^{-1}$): 3250–3050 (br), 1400, 1180.

MS (m/e): 330 (13%), 225 (100%).

Anal. Calcd. for C$_{10}$H$_7$BrN$_2$O$_2$S$_2$: C, 36.26; H, 2.13, N, 8.46%. Found: C, 36.50, H, 2.27, N. 8.13%.

EXAMPLE 7

4-[(5-Fluoro-2-benzofuranyl)methyl]-3H-1,2,3,5-oxathiadiazole 2-Oxide Scheme 3

Step (1) Preparation of 3-(4-Fluorophenoxy)-2-chloro-1-propene

According to the procedure of W. K. Anderson et al., J. Chem. Soc., Perkin 1,1 (1976), a mixture of 4-fluorophenol (20.0 g, 0.178 mol) and K$_2$CO$_3$ (27.3 g, 0.196 mol) in acetone (250 mL) was heated at reflux for 1 hour. 2,3-Dichloro-1-propene was added, and the resulting mixture was refluxed for 2 days, cooled, and concentrated. The mixture was diluted with H$_2$O, and extracted with ether (3×150 mL). The ethereal extracts were dried (MgSO$_4$) and concentrated to give a brown oil. Distillation under high vacuum gave 26.4 g (79%) of product as a colorless liquid.

NMR (CDCl$_3$, 200 MHz): δ 4.55 (d, J=1.6, 2H), 5.45 (d, J=1.0, 1H), 5.56 (dd, J=1.6, 1.0, 1H), 6.80–7.10 (m, 4H).

Step (2) Preparation of 2-(2-Chloro-1-propen-3-yl)-4-fluorophenol

According to the procedure of W. K. Anderson, et al., J. Chem. Soc., Perkin 1, 1 (1976), a mixture of 3-(4-fluorophenoxy)-2-chloro-1-propene (26.4 g, 0.141 mol) and N,N-diethylaniline (117 mL) was heated at 210°–215° C. for 2 days. The mixture was cooled, diluted with ether, and extracted with 10% HCl. The ethereal layer was dried (MgSO$_4$) and concentrated to give a brown oil. Distillation under high vacuum gave 20.9 g (86%) of product as a colorless liquid.

NMR (CDCl$_3$, 200 MHz): δ 3.62 (s, 2H), 5.15 (d, J=1.3, 1H), 5.28 (d, J=1.3, 1H), 6.72 (dd, J=8.6, 4.8, 1H), 6.85 (m, 2H).

Step (3) Preparation of 5-Fluoro-2-methylbenzofuran

According to the procedure of W. K. Anderson, et al., J. Chem. Soc., Perkin, 1, 1 (1976), a mixture of 2-(2-chloro-1-propen-3-yl)-4-fluorophenol (20.9 g, 0.112 mol) and concentrated hydrochloric acid (114 mL) was heated at 85°–89° C. for 24 hours. The mixture was cooled and diluted with ether. The ethereal layer was separated and washed with H$_2$O, 5% KOH, and H$_2$O, dried (MgSO$_4$), and concentrated to give 12.40 g (74%) of product as a brown oil.

NMR (CDCl$_3$, 200 MHz): δ 2.47 (s, 3H), 6.35 (s, 1H), 6.90 (d, J=8.5, 1H), 7.13 (dd, J=8.5, 2.5, 1H), 7.32 (dd, J=4.1, 2.5, 1H).

(4) Preparation of 4-[(5-Fluoro-2-benzofuranyl)methyl]-3H-1,2,3,5-oxathiadiazole 2-Oxide According to Scheme III, illustrated by Example 6, steps 3 to 6, 5-fluoro-2-methylbenzofuran was processed to obtain the desired product, m.p. 144°–145° C.

NMR (CDCl$_3$, 200 MHz): δ 4.05 (s, 2H), 7.1–7.7 (m, 5H).

MS (m/e): 236.

Anal. Calcd. for C$_{10}$H$_8$N$_2$O$_3$S:C, 50.55; H, 3.39; N, 11.87%. Found: C, 50.76; H, 3.38; N, 11.63%.

EXAMPLE 9

4-(Cyclohexylmethyl)-3H-1,2,3,5-oxathiadiazole 2-Oxide

Scheme 8

Step (1) Preparation of Cyclohexylacetonitrile

A solution of the cyclohexylacetic acid (20.0 g, 141 mmol) in CH$_2$Cl$_2$ (80 mL) was heated to reflux and a solution of chlorosulfonyl isocyanate (20.9 g, 148 mmol) in CH$_2$Cl$_2$ (18 mL) was added dropwise over 40 minutes. After the addition was complete, stirring was continued at reflux for 65 minutes. The mixture was cooled to 0° C., and DMF (21.1 g, 288 mmol) was added dropwise. The mixture was allowed to warm to room temperature and stirred 18 hours. The mixture was poured over ice, the organic layer separated, and the aqueous layer extracted with CH$_2$Cl$_2$ (50 mL). The combined organic layers were washed with water (3×50 mL), brine, dried (Na$_2$SO$_4$), filtered through a plug of Florosil and concentrated. The nitrile was obtained as 14.6 g (85%) of an oil of sufficient purity for use in the next reaction.

NMR (DMSO-$d_6$, 200 MHz): δ 1.10 (m, 5H), 1.62 (m, 6H), 2.40 (d, J=7.0, 2H).

Step (2) Preparation of N'-Hydroxy-cyclohexylethanimidamide

Hydroxylamine hydrochloride (10.8 g, 155 mmol) was added in one portion to a solution of NaOMe, freshly prepared from sodium (3.57 g, 155 mmol) in methanol (400 mL). The resulting mixture was stirred for 1 hour at room NMR(DMSO-$d_6$, 400 MHz): δ 4.25 (s, 2H), 6.81 (s, 1H), 7.11 (ddd, J=9.2, 8.7, 2.7, 1H), 7.43 (dd, J=8.9, 2.7, 1H), 7.57 (dd, J=8.7, 4.1, 1H), 11.61 (br s, 1H).

IR (KBr, cm$^{-1}$): 1615, 1605.

MS (m/e): 254 (38%), 149 (100%).

Anal. Calcd. for $C_{10}H_7FN_2O_3S$: C, 47.24; H, 2.78; N. 11.02%. Found: C, 47.13, H, 2.94; N, 11.00%.

EXAMPLE 8

4-[(3-Benzofuranyl)methyl]-3H-1,2,3,5-oxathiadiazole 2-Oxide

Scheme 2

Step (1) Preparation of 3-Benzofuranylacetonitrile

To a stirred mixture of hexane washed sodium hydride (2.21 g, 0.046 mol, 50%/mineral oil) in THF (125 mL), was added diethyl cyanomethylphosphonate (8.15 g, 0.046 mol) dropwise. The reaction was stirred at room temperature for ½ hour, 3-coumaranone (sublimed) (5.6 g, 0.042 mol) in THF (100 mL) was added dropwise at 0° C., and the reaction mixture was stirred at room temperature overnight. The mixture was diluted with water (300 mL), and extracted with ether (800 mL). The extracts were washed with brine (2×100 mL), dried (MgSO$_4$), and concentrated to yield 6.67 g (100%) of the product as an off-white solid.

NMR (CDCl$_3$, 200 MHz): δ 3.77 (s, 2H), 7.2–7.9 (m, 5H).

Step (2) Preparation of 4-[(3-Benzofuranyl)methyl]-3H-1,2,3,5-oxathiadiazole 2-Oxide According to Scheme I illustrated by Example 4, 3-benzofuranylacetonitrile was converted to the desired product as beige crystals, m.p. 138.5°–140° C. temperature. Cyclohexylacetonitrile (14.7 g, 120 mmol) was added in one portion and the resulting mixture was heated to reflux for 12 hours. The mixture was cooled to room temperature and concentrated to give a yellow solid. The solid was collected by filtration, washed with water, EtOAc/hexane (2:8), and dried in vacuo to give 7.4 g (40%) of the product of sufficient purity for use in the next reaction.

NMR (DMSO-$d_6$, 200 MHz): δ 0.85 (m, 2H), 1.10 (m, 3H), 1.64 (m, 6H), 1.80 (d, J=7.0, 2H), 5.25 (br s, 2H), 8.30 (br s, 1H).

Step (3) Preparation of 4-(Cyclohexylmethyl)-3H-1,2,3,5-oxathiadiazole 2-Oxide

A partial suspension of N'-hydroxy-cyclohexylethanimidamide (7.40 g, 47.4 mmol) in CH$_2$Cl$_2$ (500 mL) was treated with pyridine (18.76 g, 237 mmol) at room temperature. The resulting solution was cooled to 0° C. and treated with thionyl chloride (7.34 g, 61.7 mmol). The mixture was stirred for 1 hour at 0° C., diluted with water (200 mL), and the layers were separated. The organic layer was washed with water (200 mL), brine, dried (Na$_2$SO$_4$), and concentrated in vacuo to give an orange oil. The oil was triturated with hexane to give a yellow solid which was collected by filtration and dried in vacuo at 60° C. to give 2.58 g (26%) of the product, m.p. 86°–88° C.

NMR (DMSO-$d_6$, 400 MHz): δ 0.96 (m, 2H), 1.15 (m, 3H), 1.64 (m, 6H), 2.41 (d, J=7.0, 2H), 11.32 (br s, 1H).

IR (KBr, cm $^{-1}$): 3120, 2925, 2850, 1420, 1200.

MS (m/e): 120 (100%).

Anal. Calcd. for $C_8H_{14}N_2O_2S$: C, 47.50; H, 6.98; N, 13.85%. Found: C, 47.63; H, 6.97; N, 13.48%.

EXAMPLE 10

4-[(5-Chloro-3-benzofuranyl)methyl]-3H-1,2,3,5-oxathiadiazole 2-Oxide

Scheme II

Step (1) Preparation of Methyl 5-Chloro-2-methoxybenzoate

A mixture of 5-chlorosalicylic acid (20.0 g, 0.116 mol), potassium carbonate (40.3 g, 0.290 mol), and dimethyl sulfate (36.5 g, 0.290 mol) in acetone (300 mL) was heated at reflux for 18 hours. The mixture was cooled, concentrated, diluted with H$_2$O, and extracted with ethyl acetate (3×150 mL). The extracts were washed with H$_2$O and saturated NaCl, dried (MgSO$_4$), and concentrated to give 23.10 g (99%) of product as a brown oil.

NMR (CDCl$_3$, 200 MHz): δ 3.89 (s, 6H), 6.93 (d, J=8.9, 1H), 7.44 (dd, J=8.9, 3.0, 1H), 7.85 (d, J=3.0, 1H).

Step (2) Preparation of 5-Chloro-2-methoxybenzoic Acid

To a stirred solution of methyl 5-chloro-2-methoxybenzoate (23.1 g, 0.115 mol) in dioxane (300 mL) was added 2.5N NaOH (230 mL). The resulting mixture was stirred at room temperature for 4 hours, concentrated, diluted with H$_2$O, and acidified with 2N HCl. 19.70 g (91%) of the desired product was collected by filtration as a white solid.

NMR (CDCl$_3$, 200 MHz): δ 4.08 (s, 3H), 7.00 (d, J=8.9, 1H), 7.53 (dd, J=8.9, 2.6, 1H), 8.15 (d, J=2.6, 1H).

Step (3) Preparation of 5-Chloro-2-methoxybenzoyl Chloride

A mixture of 5-chloro-2-methoxybenzoic acid (5.00 g, 26.8 mmol) and thionyl chloride (6.38 g, 53.6 mmol) was heated at reflux for 3 hours, cooled, and concentrated. The product was washed with CCl$_4$ and dried under high vacuum to give 5.37 g (98%) of a white solid.

NMR (CDCl$_3$, 200 MHz): δ 3.39 (s, 3H), 6.96 (d, J=8.8, 1H), 7.55 (dd, J=8.8, 2.4, 1H), 8.05 (d, J=2.4, 1H).

IR (CHCl$_3$, cm$^{-1}$): 3030, 1770, 1270.

Step (4) Preparation of 5-Chloro-3-benzofuranone

According to the procedure of M. E. Jung et al., J. Org. Chem., 53, 423 (1988), a solution of diazomethane in ether [prepared from N-methyl-N-nitroso-p-toluenesulfonamide (5.8 g, 0.026 mol) and potassium hydroxide (2.9 g, 0.052 mol) in H$_2$O (7 mL), ethanol (10 mL), and ether (70 mL) utilizing a mini-Diazald ® apparatus] was added to 5-chloro-2-methoxybenzoyl chloride (2.0 g, 0.010 mol). The resulting mixture was stirred for 30 minutes, concentrated, and acetic acid (20 mL) was added. After 15 minutes, the mixture was concentrated to give 1.6 g (97%) of the product as an orange solid.

NMR (CDCl$_3$, 200 MHz): δ 4.68 (s, 2H), 7.11 (d, J=8.9, 1H), 7.57 (dd, J=8.9, 2.5, 1H), 7.64 (d, J=2.5, 1H).

Step (5) Preparation of 4-[(5-Chloro-3-benzofuranyl)methyl]-3H-1,2,3,5-oxathiadiazole 2-Oxide According to Scheme II, illustrated by Example 2, step 4 to step 6, 5-chloro-3-benzofuranone was processed to the desired product as a brown solid, m.p. 140°–141®C.

NMR (DMSO-$d_6$, 400 MHz): δ 4.07 (s, 2H), 7.36 (dd, J=8.8, 2.2, 1H), 7.63 (d, J=8.8, 1H), 7.68 (d, J=2.2, 1H), 8.00 (s, 1H), 11.51 (s, 1H).

IR (KBr, cm$^{-1}$): 3120 (broad), 1630.

MS (m/e): 270 (7.8%), 164 (100%), 206, (M+$SO_2$, 5.6%), 191 (M+, —$NHSO_2$—, 5.4%).

Anal. Calcd. for $C_{10}H_7ClN_2O_3S$: C, 44.37; H, 2.61; N, 10.35%. Found: C, 44.16; H, 2.51; N, 10.27%.

EXAMPLE 11

4-[(5-Bromo-3-benzofuranyl)methyl]-3H-1,2,3,5-oxathiadiazole 2-Oxide

Scheme II

According to Scheme II, illustrated by Example 10, 5-bromosalicylic acid was processed to the desired product as a white solid, m.p. 144°–145° C.

NMR (DMSO, 400 MHz): δ 4.07 (s, 2H), 7.47 (dd, J=8.7, 1.9, 1H), 7.58 (d, J=8.7, 1H), 7.83 (d, J=1.9, 1H), 7.98 (s, 1H), 11.51 (s, 1H).

IR (KBr, cm$^{-1}$): 3120, 1610, 1400, 1200.

MS (m/e): 314 (M+, 10.3%), 2.50 (7%), 235 (8.6%), 209 (100%), 156 (14%), 130 (12.5%), 102 (50.5%).

Anal. Calcd. for $C_{10}H_7BrN_2O_3S$: C, 38.11; H, 2.24; N. 8.89%. Found: C, 37.99; H, 2.15; N, 8.84%.

EXAMPLE 12

4-[(1,2,3,4-Tetrahydro-2-naphthalenyl)methyl]-3H-1,2,3,5-oxathiadiazole 2-Oxide

Scheme VIa

Step (1) Preparation of 1,2,3,4-Tetrahydro-2-naphthalenylacetonitrile 3.4-Dihydro-2-naphthalenylacetonitrile (11.0 g, 0.065 mol, prepared by the process of Example 3, Step 1) was hydrogenated in absolute ethanol (400 mL) with 10% palladium catalyst/carbon (1.1 g) for 6 hours, filtered through solka floc, and concentrated under reduced pressure to yield 10.6 g (95%) of product as a green oil.

NMR (CDCl$_3$, 200 MHz): δ 1.56 (m, 1H), 2.0–2.3 (m, 2H), 2.45 (d, J=7.0, 2H), 2.8–3.1 (m, 4H), 7.11 (br s, 4H).

Step (2) Preparation of 4-[(1,2,3,4,-Tetrahydro-2-naphthalenyl)methyl]-3H-1,2,3,5-oxathiadiazole 2-Oxide According to Scheme VIa, illustrated by Example 3, Steps 2 and 3, 1,2,3,4-tetrahydro-2-naphthalenylacetonitrile was processed to the desired product as a white solid, m.p. 123°–124° C.

NMR (CDCl$_3$, 200 MHz): δ 1.5 (m, 1H), 1.9–2.3 (m, 2H), 2.65 (d, J=6.8, 2H), 2.75–3.05 (m, 4H), 7.08 (br s, 4H).

MS (m/e): 250.

Anal. Calcd. for $C_{12}H_{14}N_2O_2S$: C, 57.58; H, 5.64; N, 11.19%. Found: C, 57.32; H, 5.81; N, 11.18%.

EXAMPLE 13

4-[(6-Chloro-3-benzofuranyl)methyl]-3H-1,2,3,5-oxathiadiazole 2-Oxide

According to Scheme II, illustrated by Example 2, 4-chlorosalicylic acid was processed to the desired product, m.p. 161–162 (dec.).

NMR (DMSO-$d_6$, 400 MHz): δ 4.07 (t, J=1.0, 2H), 7.34 (dd, J=8.3, 1.8, 1H), 7.61 (d, J=8.3, 1H), 7.78 (d, J=1.8, 1H) 7.98 (s, 1H), 11.50 (br s, 1H).

IR (KBr, cm$^{-1}$): 3400, 3140.

MS(m/e): 270 (12%), 165 (100%).

Anal. Calcd. for $C_{10}H_7ClN_2O_3S$: C, 44.37; H, 2.61; N, 10.35%. Found: C, 44.32; H, 2.74; N, 10.28%.

EXAMPLE 14

4-[(5,7-Dichloro-3-benzofuranyl)methyl]-3H-1,2,3,5-oxathiadiazole 2-Oxide

According to Scheme II, illustrated by Example 2, 3,5-dichlorosalicylic acid was processed to the desired product as a white solid, m.p. 170°–172° C. (dec.).

NMR (DMSO-$d_6$, 400 MHz): δ 4.10 (m, 2H), 7.61 (d, J=2.0, 1H), 7.70 (d, J=2.0, 1H), 8.14 (s, 1H), 11.51 (br s, 1H).

IR (KBr, cm$^{-1}$): 3240 (NH).

MS (m/e): 305 (9%), 199 (100%).

Anal. Calcd. for $C_{10}H_6Cl_2N_2O_3S$: C, 39.36; H, 1.98; N, 9.18%. Found: C, 39.28; H, 2.03; N, 9.20%.

EXAMPLE 15

4-[(5-Methyl-3-benzofuranyl)methyl]-3H-1,2,3,5-oxathiadiazole 2-Oxide

According to Scheme II, illustrated by Example 10, 5-methylsalicylic acid was processed to the desired product as an orange-white solid, m.p. 152°–153° C.

NMR (DMSO-$d_6$, 400 MHz): δ 2.37 (s, 3H), 3.00 (s, 2H), 7.13 (dd, J=8.5, 1.3, 1H), 7.38 (d, J=1.3, 1H), 7.45 (d, J=8.5, 1H), 7.86 (s, 1H), 11.47 (s, 1H).

IR (KBr, cm$^{-1}$: 3120 (broad), 16100, 1400.

MS (m/e): 250 (M+, 14.40%), 145 (M+, 100%).

Anal. Calcd. for $C_{11}H_{10}N_2O_3S$: C, 52.79; H, 4.03; N, 11.19%. Found: C, 52.60; H, 3.82; N, 11.09%.

EXAMPLE 16

4-[(2,3-Dihydro-1H-inden-5-yl)methyl]-3H--1,2,3,5-oxathiadiazole 2-Oxide

Scheme V

Step (1) Preparation of 5-Chloromethylindan

A mixture of indan (50.0 g, 0.423 mol), paraformaldehyde (23.3 g), concentrated HCl (74 mL), 85% $H_3PO_4$ (33 mL), and acetic acid (54 mL) was heated at 95° C. for 6 hours. The mixture was cooled and diluted with ether (200 mL). The organic phase was separated and washed with $H_2O$ (2×200 mL), saturated aqueous $NaHCO_3$ (200 mL), $H_2O$ (200 mL), dried (MgSO$_4$), and concentrated. The crude product was distilled under high vacuum (0.8 mm) to give 35.2 g (50%) as a colorless oil, b.p. 89° C.

NMR (CDCl$_3$, 200 MHz): δ 2.08 (m, 2H), 2.90 (m, 4H), 4.57 (s, 2H), 7.19 (m, 3H).

Step (2) Preparation of 5-Indanylacetonitrile

To a stirred, partial solution of NaCN (11.4 g, 0.232 mol) in DMSO 75 mL) was added 5-chloromethylindan (35.2 g, 0.211 mol) dropwise over 45 minutes. (The internal temperature was maintained below 65° C.). The resulting mixture was stirred at room temperature overnight. $H_2O$ (250 mL) was added and the mixture was extracted with ether. The organic phase was washed with $H_2O$ (200 mL), 6N HCl (100 mL), $H_2O$ (200 mL), saturated aqueous $NaHCO_3$ (100 mL), and saturated aqueous NaCl, dried (MgSO$_4$), and concentrated. The crude product was distilled under reduced pressure (0.6 mm) to give 28.1 g (85%) as a colorless oil, b.p. 131°) C.

NMR (CDCl$_3$, 200 MHz): δ 2.10 (q, J=7.3, 2H), 2.90 (t, J=7.3, 4H), 3.70 (s, 2H), 7.19 (m, 3H).

IR (CCl$_4$, cm$^{-1}$): 2250 (CN).

Step (3) Preparation of N'-Hydroxy-5-indanylethanimidamide

A stirred mixture of NaOMe (25 wt % in MeOH, 16.0 mL, 0.070 mol), hydroxylamine hydrochloride (4.9 g, 0.070 mol), and MeOH (60 mL) was heated under reflux for 30 minutes. 5-Indanylacetonitrile (10.0 g, 0.063 mol) was added and heating was continued for 18 hours. The mixture was cooled, concentrated, and partitioned between H$_2$O and ether. The organic phase was dried (MgSO$_4$) and concentrated to give a yellow oil: 11.4 g. The crude product was purified by flash chromatography (eluant 20% EtOAc/hexane; 60% EtOAc/hexane) and recrystallized from ether/hexane to give 6.5 g (54%) of a pale yellow solid, m.p. 60° C.

NMR (CDCl$_3$, 200 MHz): δ 2.06 (m, 2H), 2.88 (t, J=7.5, 4H), 3.43 (s, 2H), 4.51 (br s, 2H), 6.40 (br s, 1H), 7.14 (m, 3H).

Step (4) Preparation of 4-[(2,3-Dihydro-1H-inden-5-yl)methyl]-3H-1,2,3,5-oxathiadiazole 2-Oxide To a cooled (0° C.), stirred mixture of N'-hydroxy-5-indanylethanimidamide (6.5 g, 0.0342 mol), pyridine (5.4 g, 0.0683 mol), and CH$_2$Cl$_2$ (35 mL), was added a solution of thionyl chloride (4.5 g, 0.0376 mol) in CH$_2$Cl$_2$ (10 mL) over 20 minutes. Stirring was continued for 20 minutes and the mixture was concentrated. H$_2$O (100 mL) was added and the solid was collected by filtration. Recrystallization from ether (3 times) gave 720 mg (9%) as pale yellow needles, m.p. 122°-123° C.

NMR (CDCl$_3$, 400 MHz): δ 2.07 (m, 2H), 2.89 (t, J=7.4, 4H), 3.84 (d, J=15.8, 1H), 3.98 (d, J=15.8, 1H), 7.02 (d, J=7.6, 1H), 7.05 (br s, 1H), 7.12 (s, 1H), 7.21 (d, J=7.6, 1H).

IR (KBr, cm$^{-1}$): 3120 (NH).

MS (m/e): 236 (17%), 131 (100%).

Anal. Calcd. for C$_{11}$H$_{12}$N$_2$O$_2$S: C, 55.91; H, 5.12; N, 11.85%. Found: C, 55.74; H, 5.06; N, 11.81%.

EXAMPLE 17

4-[(5-Chloro-2-benzo[b]thienyl)methyl]-3H-1,2,3,5-oxathiadiazole 2-Oxide

According to Scheme III, illustrated by Example 6, 4-chlorothiophenol was processed to the desired product, m.p. 155°-156° C.

NMR (DMSO-d$_6$, 400 MHz): δ 4.32 (s, 2H), 7.33 (s, 1H), 7.36 (dd, J=8.6, 2.1, 1H), 7.92 (d, J=2.1, 1H), 7.97 (d, J=8.6, 1H).

IR (KBr, cm$^{-1}$): 3360 (NH).

MS (m/e): 286 (14%), 181 (100%).

Anal. Calcd. for C$_{10}$H$_7$ClN$_2$O$_2$S$_2$: C, 41.89; H, 2.46; N, 9.77%. Found: C, 42.11; H, 2.74; N, 9.54%.

EXAMPLE 18

4-(Benzo[b]thien-2-ylmethyl)-3H-1,2,3,5-oxathiadiazole 2-Oxide

According to Scheme III, illustrated by Example 6, thiophenol was processed to the desired product as a brown solid, m.p. 127°-129° C.

NMR (DMSO-d$_6$, 400 MHz): δ 4.30 (s, 2H), 7.34 (m, 3H), 7.80 (dd, J=6.9, 1.7, 1H), 7.92 (d, J=7.3, 1H), 11.58 (br s, 1H).

Anal. Calcd. for C$_{10}$H$_8$N$_2$O$_2$S$_2$: C, 47.60; H, 3.20; N, 11.10%. Found: C, 47.41; H, 3.48; N, 11.27%.

EXAMPLE 19

4-[(5-Fluoro-2-benzo[b]thienyl)methyl]-3H-1,2,3,5-oxathiadiazole 2-Oxide

According to Scheme III, illustrated by Example 6, 4-fluorothiophenol was processed to the desired product as an off-white solid, m.p. 157° C. (dec.).

NMR (CDCl$_3$, 200 MHz): δ 4.30 (s, 2H), 7.2 (m, 1H), 7.34 (s, 1H), 7.66 (m, 1H), 7.98 (m, 1H).

MS (m/e): 270.

Anal. Calcd. for C$_{10}$H$_7$FN$_2$O$_2$S$_2$: C, 44.44; H, 2.61; N, 10.36%. Found: C, 44.46; H, 2.73; N, 10.02%.

EXAMPLE 20

4-[(Benzo[b]thien-3-yl)methyl]-3H-1,2,3,5-oxathiadiazole 2-Oxide

According to Scheme V, illustrated by Example 16, thianaphthene was processed to the desired product as a beige solid, m.p. 134°-136° C.

NMR (CDCl$_3$, 400 MHz): δ 4.14 (d, J=16.4, 1H), 7.37 (s, 1H), 7.40 (m, 2H), 7.75 (dd, J=7.0, 1.7, 1H), 7.88 (dd, J=7.1, 1.5, 1H).

IR (KBr, cm$^{-1}$): 3300 (NH).

Anal. Calcd. for C$_{10}$H$_8$N$_2$O$_2$S$_2$: C, 47.60; H, 3.20; N, 11.10%. Found: C, 47.50; H, 3.26; N, 11.15%.

EXAMPLE 21

4-[(2-Benzofuranyl)methyl]-3H-1,2,3,5-oxothiadiazole 2-Oxide

According to Scheme V, illustrated by Example 16, benzofuran was processed to the desired product as pale pink needles, m.p. 133°-135° C.

NMR (DMSO-d$_6$, 400 MHz): δ 4.24 (s, 2H), 6.80 (s, 1H), 7.23 (ddd, J=7.4, 7.4, 1.2, 1H), 7.28 (ddd, J=7.4, 7.4, 1.4, 1H), 7.53 (dd, J=7.4, 1.4, 1H), 7.61 (dd, J=7.4, 1.2, 1H).

IR (KBr, cm$^{-1}$): 3120 (NH).

MS (m/e): 236 (20%), 131 (100%).

Anal. Calcd. for C$_{10}$H$_8$N$_2$O$_3$S: C, 50.84; H, 3.41; N, 11.86%. Found: C, 50.91; H, 3.54; N, 11.57%.

EXAMPLE 22

4-[[(3,4-Methylenedioxy)phenyl]methyl]-3H-1,2,3,5-oxathiadiazole 2-Oxide

According to Scheme I, as illustrated by Example 4, 3,4-(methylenedioxyl)phenylacetonitrile was processed to the desired product as a brown solid, m.p. 132°-133° C.

NMR (DMSO-d$_6$, 400 MHz): δ 3.83 (s, 2H), 5.99 (s, 2H), 6.76 (dd, J=7.9, 1.6, 1H), 7.86 (d, J=1.6, 1H), 7.87 (d, J=7.9, 1H), 11.38 (s, 1H).

IR (KBr, cm$^{-1}$): 3105, 2910, 1610.

MS (m/e): 240 (62%), 135 (100%).

Anal. Calcd. for C$_9$H$_8$N$_2$O$_4$S: C, 44.99; H, 3.36; N, 11.66%. Found: C, 45.12; H, 3.37; N, 11.34%.

The blood glucose lowering activity of the compounds of this invention was demonstrable in experiments using diabetic (db/db) mice. The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia. Furthermore, the db/db mouse will eventually develop some of the long-term complications that have been associated with diabetes mellitus.

[See Coleman *Diabetes* 31 (suppl. 1), 1 (1982).] In spite of these commonalities, the acute administration of sulfonylureas (even at extremely high dosages) will not reduce the hyperglycemia of the db/db mouse. [See Tutwiler et al, *Diabetes* 27, 856 (1978).] The ability of a few other hypoglycemic agents to be effective in this species suggests that the other agents have mechanisms of action which are different from that of the sulfonylureas [ibid; Lee et al, *Diabetes* 31:12 (1982); Chang et al, *Diabetes* 32, 830 (1983); Hosokawa et al, *Diabetes* 34, 267 (1985)]. Such compounds, therefore, are more likely to be efficacious in the population of Type II diabetic patients that do not respond to sulfonylurea therapy. The experimental results are exemplified hereinbelow after the listing of the following general procedure pertaining to these experiments.

POSTPRANDIAL ASSAY PROCEDURE

On the morning of Day 1, 35 mice [male db/db (C57BL/KsJ), Jackson Laboratories, 2 to 7 months of age and body weight 35 to 60 g]were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbot VP Analyser. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels:

| Group A: | Vehicle control | N = 6 |
|---|---|---|
| Group B: | Positive control (ciglitazone) | N = 4 |
| Group C: | 1st Test drug | N = 4 |
| Group D: | 2nd Test drug | N = 4 |
| Group E: | 3rd Test drug | N = 4 |
| Group F: | 4th Test drug | N = 4 |
| Group H: | 5th Test drug | N = 4 |

On the afternoon of Days 1, 2 and 3 the vehicle, control of test drugs were administered (p.o.) to the ad libitum fed mice. The positive control, ciglitazon [($\pm$)-5-[4-[(1-methylcyclohexy]methoxyl]benzyl]-thiazolidine-2,4-dione]see Fujita et al., *Diabetes* 32 804 (1983), was given by gavage at a dose of 100 mg/kg/day. The test compounds were given by gavage at a dose of 100 mg/kg/day unless otherwise noted in Table 1.

On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hours after drug administration. The plasma was separated and levels of glucose in plasma determined by the Abbot VP Analyser.

For each mouse, the percent change of its plasma glucose level on Day 4 (mean of the 2 and 4 hour samples) from its respective level before drug administration (Day 1 baseline sample) was determined as follows:

$$\frac{\text{Mean of 2 and 4 hour Samples (Day 4)}}{\text{Baseline Sample (Day 1)}} \times 100$$

Analysis of variance followed by Dunnett's multiple comparison (one-sided) was used to estimate the degree of statistical significance of the difference between the vehicle control group and the individual drug-treated groups. A drug was considered active, at the specific dosage administered, if the difference of the plasma glucose level had a $p<0.05$.

The tabulated results in Table 1 show that the oxathiadiazoles of this invention show the property that they lower blood glucose levels in the diabetic (db/db) mice using the Postprandial Assay Procedure. The actual difference between the mean percent change of the vehicle and the drug-treated group is reported in Table 1.

TABLE 1

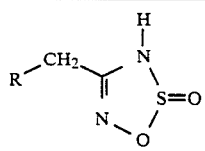

| Example # | R | Process Scheme | m.p. °C. | Dose mg/kg/day | % Change from Vehicle in Postprandial Plasma Glucose |
|---|---|---|---|---|---|
| 1 | [1-chloro-naphthalen-2-yl] | VII | 90.5–91.5 | 20 | −27 |
| 2 | [7-chloro-benzofuran-2-yl] | II | 160–162 | 20 | −26 |

TABLE 1-continued
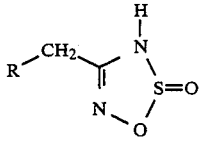
| Example # | R | Process Scheme | m.p. °C. | Dose mg/kg/day | % Change from Vehicle in Postprandial Plasma Glucose |
|---|---|---|---|---|---|
| 3 | 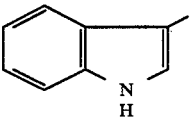 | VI | 118–120.5 | 100<br>20 | −55<br>−23 |
| 4 | 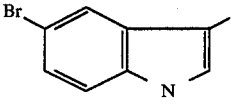 | I | 125(dec.) | 100<br>20 | −22<br>−26 |
| 5 | 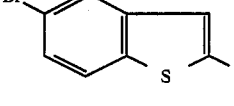 | IV | 126(dec.) | 20 | −22 |
| 6 | 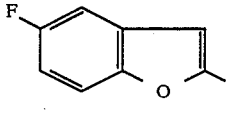 | III | 156–157 | 100<br>20 | −29<br>−20 |
| 7 | 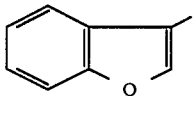 | III | 144–145 | 100<br>20 | −25<br>−18 |
| 8 | 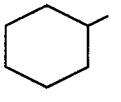 | II | 138.5–140 | 100<br>20 | −28<br>−17 |
| 9 | 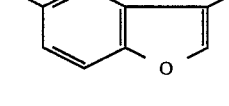 | VIII | 86–88 | 100 | −31 |
| 10 | 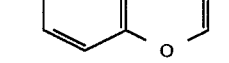 | II | 140–141 | 20 | −15 |
| 11 | 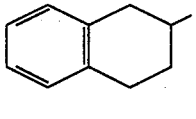 | II | 144–145 | 20 | −14 |
| 12 | 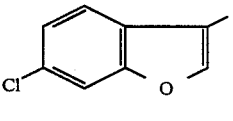 | VI | 123–124 | 100<br>20 | −22<br>−14 |
| 13 |  | II | 161–162(dec.) | 20 | −9 |

TABLE 1-continued
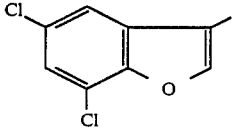
| Example # | R | Process Scheme | m.p. °C. | Dose mg/kg/day | % Change from Vehicle in Postprandial Plasma Glucose |
|---|---|---|---|---|---|
| 14 | 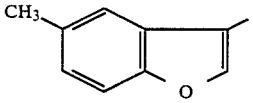 | II | 170–172 | 20 | −9 |
| 15 | 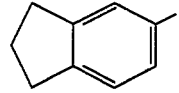 | II | 152–153 | 20 | −9 |
| 16 | 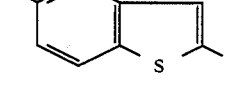 | V | 122–123 | 20 | −8 |
| 17 | 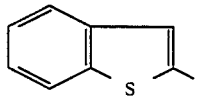 | III | 155–156 | 20 | −7 |
| 18 | 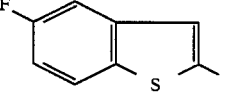 | III | 127–129 | 20 | −7 |
| 19 | 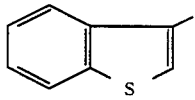 | III | 157 (dec.) | 20 | −7 |
| 20 | 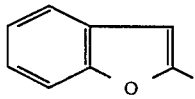 | V | 134–136 | 20 | −4 |
| 21 | 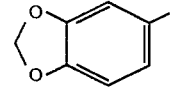 | V | 133–135 | 20 | −1 |
| 22 | | I | 132–133 | 20 | −1 |
| 23 | 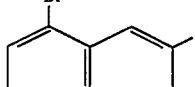 | VI | 137–139 | 5 | −40 |
| Ciglitazone (reference standard) | | | | 100 | −33 |
We claim:
1. A compound of formula (I)

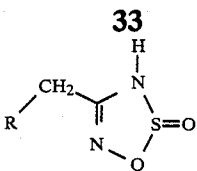
(I)

wherein R is
(a)

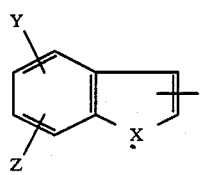

and X is NH, O, or S, and Y and Z are independently hydrogen, lower alkyl containing 1 to 6 carbon atoms, or halogen;
or R is
(b)

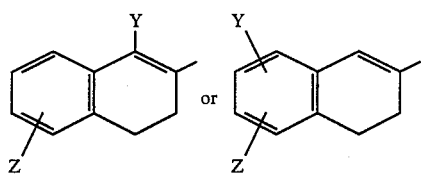

and Y and Z are as defined above;
or R is
(c)

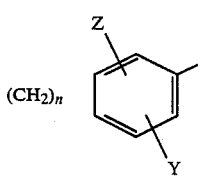

and n is 3 or 4, and Y and Z are as defined above;
or R is
(d)

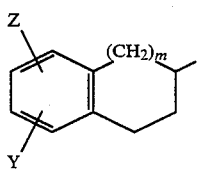

and m is 0 or 1, and Y and Z are as defined above;
or R is;
(e)

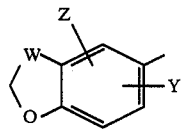

and W is CH$_2$ or O, and Y and Z are as defined above or R is cyclohexyl; or the pharmaceutically acceptable salts thereof.

2. A compound according to claim 1 of formula (II)

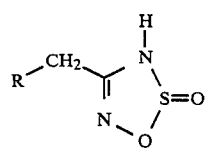
(II)

wherein R is
(a)

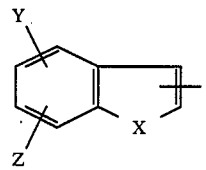

and X is NH, O, S, and Y and Z are independently hydrogen, lower alkyl containing 1 to 6 carbon atoms, or halogen;
or R is
(b)

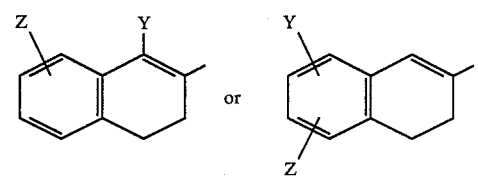

and Y and Z are as defined above; or the pharmaceutically acceptable salts thereof.

3. The compound according to claim 2 4-[(1-chloro-3,4-dihydro-2-naphthalenyl)methyl]-3H-1,2,3,5-oxathiadiazole 2-oxide or the pharmaceutically acceptable salts thereof.

4. The compound according to claim 2 4-[(7-chloro-3-benzofuranyl)methyl-3H-1,2,3,5-oxathiadiazole 2-oxide or the pharmaceutically acceptable salts thereof.

5. The compound according to claim 2 4-[(3,4-dihydro-2-naphthalenyl)methyl]-3H-1,2,3,5-oxathiadiazole 2-oxide or the pharmaceutically acceptable salts thereof.

6. The compound according to claim 2 4-(1H-indol-3-ylmethyl)-3H-1,2,3,5-oxathiadiazole 2-oxide or the pharmaceutically acceptable salts thereof.

7. The compound according to claim 2 4 -[(5-bromo-1H-indol-3-yl)methyl]-3H-1,2,3,5-oxathiadiazole 2-oxide or the pharmaceutically acceptable salts thereof.

8. The compound according to claim 2 40[(5-bromo-2-benzo[b]thienyl)methyl]-3H-1,2,3,5-oxathiadiazole 2-oxide or the pharmaceutically acceptable salts thereof.

9. The compound according to claim 2 4-[(5-fluoro-2-benzofuranyl)methyl]-3H-1,2,3,5-oxathiadiazole 2-oxide or the pharmaceutically acceptable salts thereof.

10. The compound according to claim 2 4-[(3-benzofuranyl)methyl]-3H-1,2,3,5-oxathiadiazole 2-oxide or the pharmaceutically acceptable salts thereof.

11. The compound according to claim 2 4-[(5-chloro-3-benzofuranyl)methyl]-3H-1,2,3,5-oxathiadiazole 2-oxide or the pharmaceutically acceptable salts thereof.

12. The compound according to claim 2 4-[(5-bromo-3-benzofuranyl)methyl]-3H-1,2,3,5-oxathiadiazole 2-oxide or the pharmaceutically acceptable salts thereof.

13. The compound according to claim 2 4-[(6-chloro-3-benzofuranyl)methyl]-3H-1,2,3,5-oxathiadiazole 2-oxide or the pharmaceutically acceptable salts thereof.

14. The compound according to claim 2 4-[(5,7-dichloro-3-benzofuranyl)methyl]-3H-1,2,3,5-oxathiadiazole 2-oxide or the pharmaceutically acceptable salts thereof.

15. The compound according to claim 2 4-[(5-methyl-3-benzofuranyl)methyl]-3H-1,2,3,5-oxathiadiazole 2-oxide or the pharmaceutically acceptable salts thereof.

16. The compound according to claim 2 4-8 (5-chloro-b 2-benzo[b]thienyl)methyl]-3H-1,2,3,5-oxathiadiazole 2-oxide or the pharmaceutically acceptable salts thereof.

17. The compound according to claim 2 4-(benzo[b]thien-2-ylmethyl)-3H-1,2,3,5-oxathiadiazole 2oxide or the pharmaceutically acceptable salts thereof.

18. The compound according to claim 2 4[(5-fluoro-2-benzo[b]thienyl)methyl]-3H-1,2,3,5-oxathiadiazole 2-oxide or the pharmaceutically acceptable salts thereof.

19. The compound according to claim 2 4-[(benzo[b]thien-3-yl)methyl]-3H-1,2,3,5-oxathiadiazole 2-oxide or the pharmaceutically acceptable salts thereof.

20. The compound according to claim 2 4-[(2-benzofuranyl)methyl]-3H-1,2,3,5-oxathiadiazole 2-oxide or the pharmaceutically acceptable salts thereof.

21. The compound according to claim 2 4-[(8-bromo-3,4-dihydro-2-naphthalenyl)methyl]-3H-1,2,3,5-oxathiadiazole 2-oxide or the pharmaceutically acceptable salts thereof.

22. A method of treating non-insulin dependent diabetes mellitus in humans by administering an effective amount of the compound of claim 1.

23. A pharmaceutical composition useful for treating non-insulin dependent diabetes mellitus in humans comprising an effective amount of a compound of claim 1 and a pharmaceutically acceptable carrier.

* * * * *